United States Patent
Doty

(10) Patent No.: US 6,494,901 B1
(45) Date of Patent: *Dec. 17, 2002

(54) TANNING BED

(75) Inventor: John Stephen Doty, Jonesboro, AR (US)

(73) Assignee: Sun Ergoline, Inc., Jonesboro, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/561,853

(22) Filed: Apr. 28, 2000

Related U.S. Application Data

(63) Continuation of application No. 08/963,187, filed on Nov. 3, 1997, now Pat. No. 6,139,568, which is a continuation of application No. 08/544,269, filed on Oct. 17, 1995, now Pat. No. 5,683,437.

(51) Int. Cl.[7] ................................................. A61N 5/06

(52) U.S. Cl. ............................ 607/91; 607/88; 607/90; 250/504 R

(58) Field of Search .............................. 607/80, 88–95; 362/84; 250/504 R, 493.1, 494.1; 315/324

(56) References Cited

U.S. PATENT DOCUMENTS

| | | |
|---|---|---|
| 4,095,113 A | 6/1978 | Wolff |
| 4,106,083 A | 8/1978 | Wolff |
| 4,177,384 A | 12/1979 | Wolff |
| 4,194,125 A | 3/1980 | Wolff |
| 4,196,354 A | 4/1980 | Wolff |
| 4,287,554 A | 9/1981 | Wolff |
| 4,309,616 A | 1/1982 | Wolff |
| 4,316,094 A | 2/1982 | Wolff |

(List continued on next page.)

FOREIGN PATENT DOCUMENTS

| | | |
|---|---|---|
| CH | 676428 B | 1/1991 |
| DE | 3005-487 | 8/1981 |
| DE | 3017-355 | 11/1981 |
| DE | 3037-775 | 5/1982 |
| DE | 3129-486 | 2/1983 |
| DE | 3303-794 A | 8/1984 |
| DE | 3443-045 A | 5/1986 |
| DE | 3533789 A1 | 6/1986 |
| DE | 4001-666 A | 8/1990 |
| GB | 2 239 399 A | 7/1991 |
| NL | 8503-406 A | 7/1987 |

OTHER PUBLICATIONS

Three color pages of SUNAL's 1993 Tanning Beds & Parts Catalog featuring Newline 55NL8 tanning bed.

Two color pages of SUNAL 1993 Advertisement featuring the Sunburst 24 Sei tanning bed.

*Primary Examiner*—Linda C. M. Dvorak
*Assistant Examiner*—David M. Ruddy
(74) *Attorney, Agent, or Firm*—Crutsinger & Booth

(57) ABSTRACT

Tanning bed apparatus is provided for providing a person with an artificial sun tan. The apparatus includes a lower tanning unit and an upper tanning unit that is moveable between an open and a closed position where the units together form a tanning chamber. A first longitudinally extending edge of the lower tanning unit is positioned lower than the vertical center of the tanning chamber to ease the task of entering and exiting the chamber. A second longitudinally extending edge of the lower tanning unit includes at least one tanning bulb that is positioned at or above the vertical center of the chamber to eliminate uneven tanning along one longitudinally extending edge of the user. At least one tanning bulb in the first longitudinally extending edge of the upper tanning unit is positioned at or below the vertical center of the chamber to eliminate uneven tanning along the opposite longitudinally extending edges of the user. The upper tanning unit includes two rows of tanning bulbs positioned in a staggered configuration that reduces the time required to achieve the desired level of tanning.

7 Claims, 4 Drawing Sheets

U.S. PATENT DOCUMENTS

| | | |
|---|---|---|
| 4,590,940 A | 5/1986 | Pigmans |
| 4,623,796 A * | 11/1986 | Kratz .......................... 607/91 |
| 4,651,263 A | 3/1987 | Hancock |
| 4,660,561 A | 4/1987 | Nielsen |
| 4,683,379 A | 7/1987 | Wolff |
| 4,683,886 A | 8/1987 | Kramer et al. |
| 4,703,184 A | 10/1987 | Wolff |
| 4,835,400 A | 5/1989 | Wolff |
| 4,918,319 A | 4/1990 | Kruithof |
| 5,370,673 A | 12/1994 | Angelo |
| 5,383,916 A | 1/1995 | Brown |

* cited by examiner

TANNING BED

This application is a continuation of application Ser. No. 08/963,187 filed on Nov. 3, 1997, now U.S. Pat. No. 6,139,568, which itself is a continuation of application Ser. No. 08/544,269 filed on Oct. 17, 1995, now issued as U.S. Pat. No. 5,683,437.

FIELD OF THE INVENTION

The present invention provides an apparatus for artificially tanning a person. According to one aspect of the invention, the tanning apparatus is configured for more effectively tanning the sides of a person and for easy access. According to another aspect of the invention, the tanning apparatus is provided with specially arranged ultraviolet lamps for providing an enhanced radiation energy source.

BACKGROUND OF THE INVENTION

Tanning beds making use of artificial ultra violet light are very popular, especially in the winter months when a natural tan can not be readily acquired and particularly in those areas where the summer tanning season is relatively short. Many tanning operators own a number of tanning beds for rent to the public. The length of time that a user must stay in the tanning chamber to achieve a desired tanning affect is a limiting factor on how often the beds can be rented and thus has a direct impact on profits.

A typical tanning bed has an upper tanning unit and a lower tanning unit connected by hinges so that the upper unit can be opened and a closed in a manner analogous to a clamshell In the open position, a person can enter the apparatus to lie down on the lower tanning unit In the closed position the units form an internal tanning chamber where the person to be tanned is partially surrounded by tanning lamps. The upper unit has a row of lamps that are intended to tan the upwardly facing parts of the person, and the lower unit has a row of lamps that are intended to tan the downwardly facing parts of the person.

A problem that is often encountered in prior art devices is uneven tanning along a users' sides that arises because of a break in the lamp distribution at the S sides of the chamber where the upper and lower tanning units meet when in the closed position. In a typical tanning bed, the upper and lower units meet on opposite sides of the tanning chamber near the vertical center of the chamber. Consequently, the user cannot eliminate the uneven tan by a method such as periodically alternating from lying on his or her back and stomach.

Another problem with typical tanning beds is that the upper tanning unit, when in the closed position, must provide a reasonable amount of room above the person lying in the bed. However, providing the overhead space requires that the lamps in the upper tanning unit be positioned farther away from the person than the lamps in the lower tanning unit The overhead space decreases the amount of tanning radiation that reaches the upwardly facing parts of a person, which increases the time required to achieve a desired level of exposure.

SUMMARY OF THE INVENTION

In accordance with the present invention, a tanning bed is provided that comprises an upper tanning unit and a lower tanning unit positioned on a base. The lower tanning unit has a lower radiation source positioned between a first longitudinally extending edge on one side of the lower unit and a second longitudinally extending edge on the opposite side of the lower unit has an upper radiation source that is similarly positioned between a first longitudinally extending edge on one side of the upper unit and a second longitudinally extending edge on the opposite side of the upper unit The upper tanning unit is connected to the base by a hinge mechanism and is moveable between an open and a closed position. A user accesses the tanning bed by ascending over the first longitudinal edge of the lower unit when the upper unit is in the open position In the closed position the upper and lower tanning units face each other and form a tanning chamber with the first and second longitudinal edges of the upper tanning unit positioned adjacent the first and second longitudinal edges of the lower tanning unit, respectively.

According to a first aspect of the invention, the first longitudinal edge of the lower tanning unit is positioned below the centerline of the tanning chamber to provide for easy entry and access into the tanning chamber. When in the closed position, at least one tanning lamp is positioned near the vertical center of one side of the tanning chamber, and at least one tanning lamp is positioned near the vertical center on the opposite side of the tanning chamber to eliminate uneven tanning along the user's sides. According to a second aspect of the invention, the upper tanning unit is provided with an upper radiation source comprising a first row and a second row of tanning lamps that may comprise a higher output The lamps are positioned in a staggered arrangement that minimizes the reflection and refraction losses of the radiation emitted from the lamps in the second row. The second row of lamps and the staggered arrangement result in a higher level of tanning radiation that reaches the upwardly facing parts of the person, thereby reducing the time required to achieve the desired level of exposure.

BRIEF DESCRIPTION OF THE DRAWING

The accompanying drawing is incorporated into and forms a part of the specification to illustrate at least one presently most preferred embodiment of the present invention The figures of the drawing together with the written description serve to explain the principles of the invention. The drawing is only for the purpose of illustrating examples of how the invention can be made and used and is not to be construed as limiting the invention to only the illustrated and described examples. The various advantages and features of the present invention will be apparent from consideration of the written description with the drawing, wherein.

DESCRIPTION OF A PREFERRED EMBODIMENT

Figure 1:
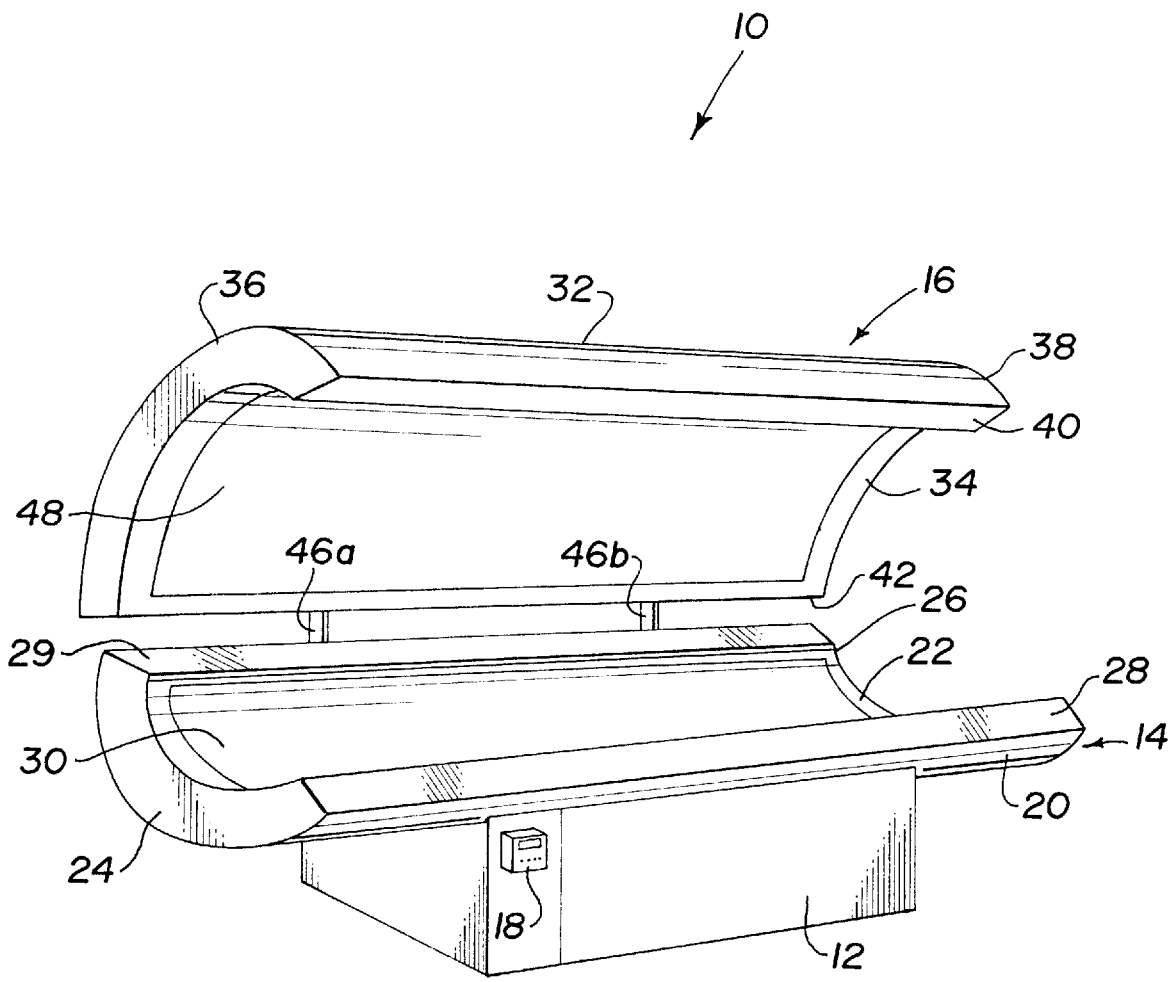
FIG. 1 is a perspective view of the preferred embodiment.

Referring now to the drawing, there is illustrated in FIG. 1 a view of the preferred embodiment of the tanning bed that is generally referred to by the reference numeral 10. The tanning bed 10 is shown in an open position and comprises a base 12, a lower tanning unit 14, and an upper tanning unit 16.

The base 12 supports the lower tanning unit 14 and the upper tanning unit 16. The base can have any suitable configuration such as the configuration generally shown in FIG. 1 and houses conventional hardware (not shown) that is used to power radiation sources in the upper and lower tanning units 14 and 16. A timer 18 can be affixed to the tanning bed 10 if desired, where it is readily accessible to the user to control the operation of the tanning bed.

The lower tanning unit 14 has an outer wall 20, an inner wall 22, a pair of oppositely disposed ends 24 and 26, a first longitudinally extending edge 28, and a second longitudinally extending edge 29. The outer wall 20 is mounted directly to the base 12 The inner wall 22 includes an upwardly facing, concave sheet 30 of ultra violet transmissive material. The term "transmissive material" as used herein refers to materials that will allow most or all of the type of radiation used in the tanning bed to be transmitted through it. A preferred transmissive material is acrylic.

The upper tanning unit 16 has an outer wall 32, an inner wall 34, a pair of oppositely disposed ends 36 and 38, a first longitudinally extending edge 40, and a second longitudinally extending edge 42. The outer wall 32 is mounted to a pair of hinge arms 46a and 46b that allows the upper tanning unit 16 to move between an open position and a closed position. The ends 36 and 38 and longitudinal edges 40 and 42 on the upper tanning unit 16 have the same lengths as the corresponding ends 24 and 26 and longitudinal edges 28 and 29 on the lower tanning unit 14. The inner wail 34 comprises a concave sheet 48 of transmissive material to shield the ultra violet lamps from the user, and to prevent the user from being injured in the event of a broken lamp.

Figure 2:
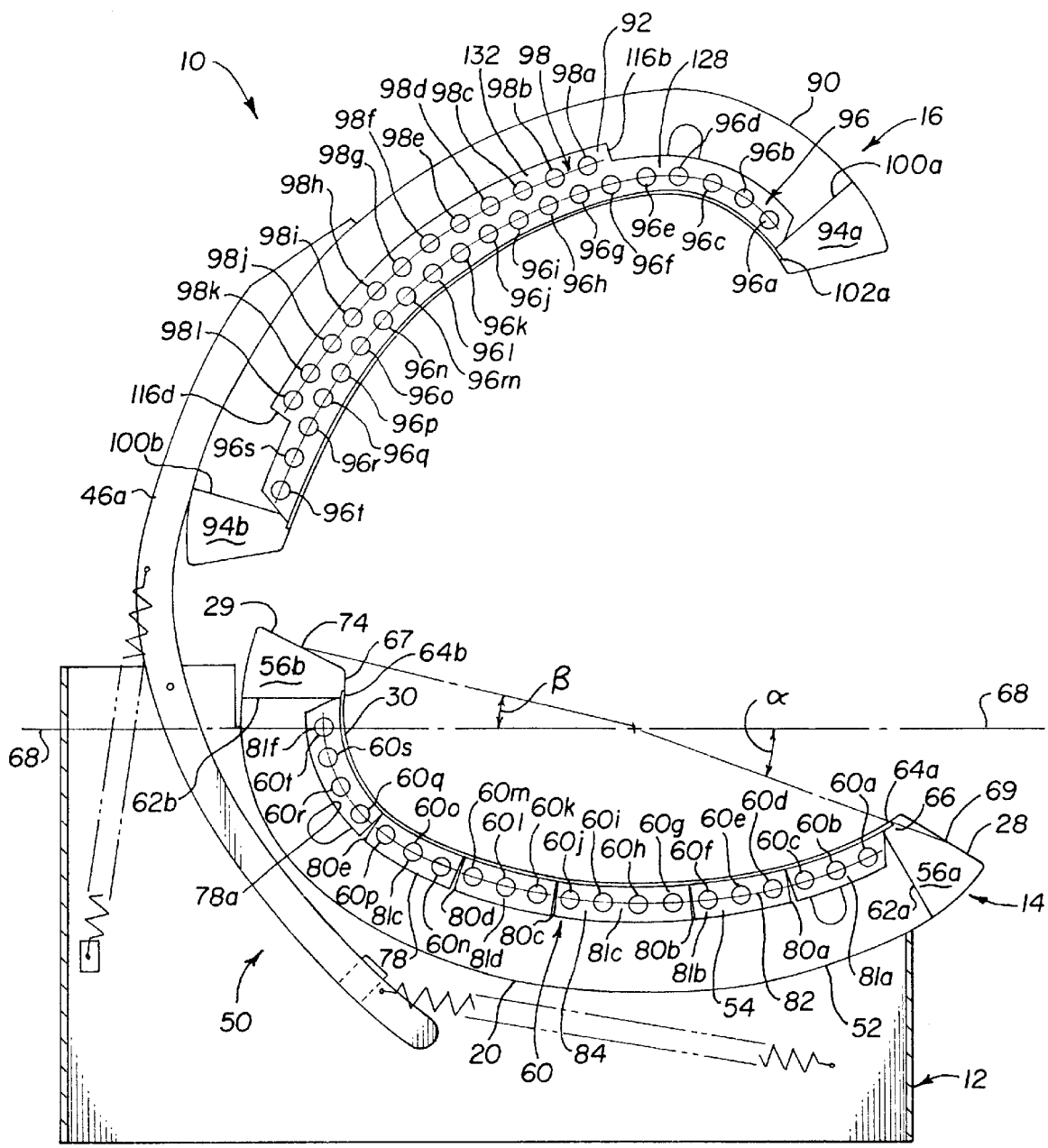
FIG. 2 is a sectional view of the preferred embodiment with the upper tanning unit in open position.

FIG. 2 is a sectional view of the preferred embodiment in the open position. The lower tanning unit 14 is mounted directly to the base 12 using any conventional fastening device The upper tanning unit 16 is connected to the base 12 by hinge arms 46a and 46b using any conventional fastening device. The hinge arms 46a and 46b are part of the hinge mechanism 50, which can be any device that permits the upper tanning unit 16 to move between an open and a closed position. An example of a suitable hinge mechanism is disclosed in U.S. Pat. No. 5,370,673, issued to Gary P. Angelo on Dec. 6, 1994, which is incorporated herein by reference in its entirety.

The lower tanning unit 14 comprises a cross member 52, a lamp chamber 54, a first extruded rail 56a and a second extruded rail 56b. In the preferred embodiment the lamp chamber 54 houses a row of tanning lamps 60, for example lamps 60a-60t that function as a radiation source. The lower tanning unit 14 is assembled by securing the first extruded rail 56a to the cross member mounting bracket 62a of the cross member 52 and the second extruded rail 56b to the cross member mounting bracket 62b of the cross member 52 using any conventional means. The first edge 64a and second edge 64b of the concave sheet 30 are secured to the extruded rails by mounting strips 66 and 67.

Longitudinal edge 28 on first extruded rail 56a includes a center point 69 positioned at an angle $\alpha$ below the horizontal centerline 68. In the preferred embodiment, the angle $\alpha$ measures from about 15° to about 45°, with about 15° to about 25° being more preferred, and with about 17.5° being most preferred. The extruded rail 56a is thus positioned in the lower right quadrant (referred to as the access quadrant hereafter) of the tanning bed 10. The extruded rail 56a is positioned in the access quadrant to ease the difficulty of ascending over the first longitudinal edge 28 when entering and exiting the tanning bed 10.

In the presently most preferred embodiment, longitudinal edge 29 on second extruded rail 56b includes a center point 74 positioned at an angle B above the horizontal centerline 68. The center point 74 is positioned this way to ensure that at least one tanning bulb (60t for example) can be positioned within about 5° of the centerline 68, and more preferably located on the centerline In the preferred embodiment the angle $\beta$ measures from about 15° to about 45°, with about 15° to about 25° being more preferred, and with about 17.5° being most preferred. Furthermore, in the preferred embodiment, the angle $\beta$ is equal to angle $\alpha$ which positions the center point 69 on extruded rail 56a. When the angles $\alpha$ and $\beta$ are equal, some of the geometrical features on the upper and lower tanning units 16 and 14 are the same or similar, which can reduce tooling and manufacturing costs.

According to a further embodiment, the angle $\beta$ can measure up to about 90° above the centerline. In such an embodiment, the row of tanning lamps 60 will include additional lamps (not shown) with at least one lamp positioned within 5° of the centerline 68, and more preferably on the centerline as hereinbefore described. According to another embodiment, the angle $\beta$ can measure up to about 45° below the centerline 68. In such an embodiment, at least one lamp in the upper tanning unit 16 is positioned within 5° of centerline 68, and more preferably on the centerline, as will be described hereafter.

The cross member 52 extends from the first extruded rail 56a to the second extruded rail 56b and provides structural support and rigidity for the lower tanning unit 14. The cross member 52 is sturdy enough to support the weight of the user along with any weight from the upper tanning unit 16 that may be applied to the lower unit 14 in the event the upper unit rests on the lower unit when in the closed position. The cross member 52 has an outer wall 20 that is attached to the base 12 and an inner wall 78 that also forms part of the lamp chamber 54.

The lamp chamber 54 accommodates a row of tanning lamps 60 having tanning lamps 60a-60t and is enclosed by the first extruded rail 56a, the second extruded rail 56b, inner wall 78, and concave acrylic sheet 30. The inner wall 78 includes a surface 78a facing the lamp chamber 54 that is reflective to the type of radiation emitted from the tanning lamps. Since a person using the tanning bed 10 will lie on the concave sheet 30, the sheet material is one that will support the weight of the user. The sheet 30 can be structurally reinforced by aluminum supports (also constructed of reflector material) 80a-80e to transmit weight applied to the sheet 30 into the inner wall 78a on the cross member 52. The lamp chamber 54 may comprise a plurality of individual lamp chassis sections, for example, sections 81a-81f, if desired.

The lamp chamber 54 has a width defined by the centerline 82 that extends between the first and second extruded rails 56a and 56b, and a depth 84 defined by the distance between the inner wall 78 and the concave sheet 30. The depth of the chamber 54 is sufficient to accommodate the diameter of a 100 watt high output tanning lamp, and the length is sufficient to accommodate the desired number of lamps. In the preferred embodiment, the width accommodates twenty (20) 100 watt high output tanning lamps 60a-60t. The lamps are all preferably low pressure fluorescent and produce ultraviolet radiation between the range of 280 to 400 nanometers. The lamps are positioned on centerline 82 with lamps 60a-60o spaced from about 3° to about 5° apart on about a 31 to 32 inch radius and with lamps 60p-60t spaced from about 14° to about 17° apart on about a 7 to 8 inch radius. This spacing will leave at least a "finger width" distance between the tanning lamps to facilitate grasping the lamps during installation and removal. The lamps extend over most of the distance between oppositely disposed ends 24 and 26 of the lower tanning unit 14 (see FIG. 1), and the ends of the lamps (not shown) are mechanically and electrically connected to the lower tanning unit 14 using conventional lampholders.

The upper tanning unit comprises a cross member 90, a lamp chamber 92, a first extruded rail 94a, and a second extruded rail 94b. In the preferred embodiment the lamp chamber 92 houses a first row of tanning lamps 96 and a second row of tanning lamps 98, both of which function as a radiation source. The upper tanning unit 16 is assembled by securing the first and second extruded rails 94a and 94b to the first and second ends 100a and 100b of cross member 90 using any conventional means, and by securing the first and second edges 102a and 102b of the concave sheet 48 to the extruded rails 94a and 94b.

Figure 3:
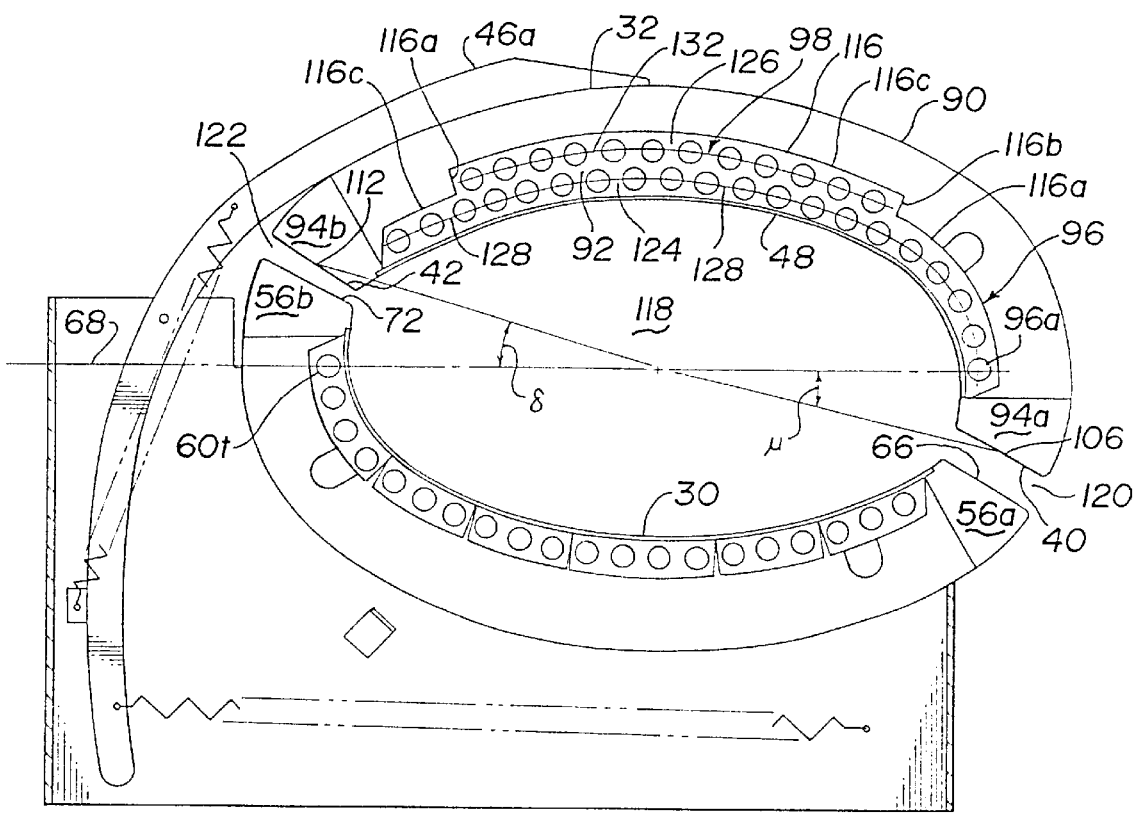
FIG. 3 is a sectional view of the preferred embodiment with the upper tanning unit in a closed position.

Referring to FIG. 3, longitudinal edge 40 on first extruded rail 94a includes a center point 106 positioned at an angle $\mu$ below the horizontal centerline 68. In the preferred embodiment, the angle $\mu$ measures from about 15° to about 45°, with about 15° to about 25° being more preferred, and with about 17.5° being most preferred. The first extruded rail 94a is positioned below the horizontal centerline 68 to ensure that at least one tanning bulb (96a for example) in the first row of lamps 96 will be positioned at or below the horizontal centerline 68.

Longitudinally extending edge 42 on second extruded rail 94b includes a center point 112 positioned at an angle 6 above the horizontal centerline 68. In the preferred embodiment the angle measures from about 15° to about 45°, with about 15° to about 25° being more preferred, and with about 17.5° being most preferred. Locating the second extruded rail 94b above the centerline 68 permits the second extruded rail 56b of lower tanning unit 14 to also be located above the centerline 68 thus positioning at least one tanning bulb (64t for example) within 5° of the centerline 68, and more preferably on the centerline 68.

According to further embodiments, the center point 112 can be positioned from about 45° in the lower left quadrant to about 90° in the upper left quadrant. This positioning corresponds to the similar positioning of center point 74 on extruded rail 56b in previously described embodiments. When the center point 112 is positioned below the centerline 68, the row of tanning lamps 96 will include additional lamps (not shown) with at least one lamp positioned within about 5° of the centerline 68, and more preferably on the centerline 68.

Cross member 90 includes an outer wall 32, and an inner wall 116, and extends from the first extruded rail 94a to the second extruded rail 94b to provide structural support and rigidity for the upper tanning unit 16. The outer wall 32 is attached to the hinge arms 46a and 46b. The hinge arms 46a and 46b support the upper tanning unit 16 above the lower tanning unit 14 with the concave sheets 30 and 48 facing each other to define a tanning chamber 118. The longitudinally extending edges 40 and 66 on first extruded rails 56a and 94a are adjacent each other and are separated by a nominal gap 120, and the longitudinally extending edges 42 and 72 on second extruded rails 56b and 94b are similarly adjacent each other and are separated by a nominal gap 122 The inner wall 116 includes five sections 116a-116e that also form part of the lamp chamber 92.

The lamp chamber 92 is enclosed by the extruded rails 94a and 94b, sections 116a-116e of inner wall 116, and concave sheet 48. The sides of sections 116a-116e facing the lamp chamber 92 are reflective to the type of radiation emitted from the tanning lamps. The lamp chamber 92 is divided into a first section 124 that contains a first row of tanning bulbs 96 and a second section 126 that contains a second row of tanning bulbs 98. The lamps are preferably low pressure fluorescent and produce ultraviolet radiation between the range of 280 to 400 nanometers. The lamps extend over most of the distance between oppositely disposed ends 36 and 38 on the upper tanning unit 116 (see FIG. 1), and the ends of the lamps (not shown) are mechanically and electrically connected to the upper tanning unit 16 using conventional lampholders.

The first section 124 of the lamp chamber 92 has a width defined by the centerline 128 that extends from one extruded rail 94a to the second extruded rail 94b and a depth defined by the distance between inner wall sections 116f and 116g and the concave sheet 48. The depth of the chamber is sufficient to accommodate a T12 100 or T12 160 watt high output tanning lamp, and the width is sufficient to accommodate the desired number of lamps. Referring back to FIG. 2, the preferred width accommodates a row of lamps 96 having twenty (20) T12 100 or T12 160 watt tanning lamps positioned on the centerline 128 with lamps (96a-96o) spaced from about 3° to about 5° apart on about a 31 to 32 inch radius and lamps (96p-96t) spaced from about 14° to about 17° apart on about a 7 to 8 inch radius.

Figure 4:
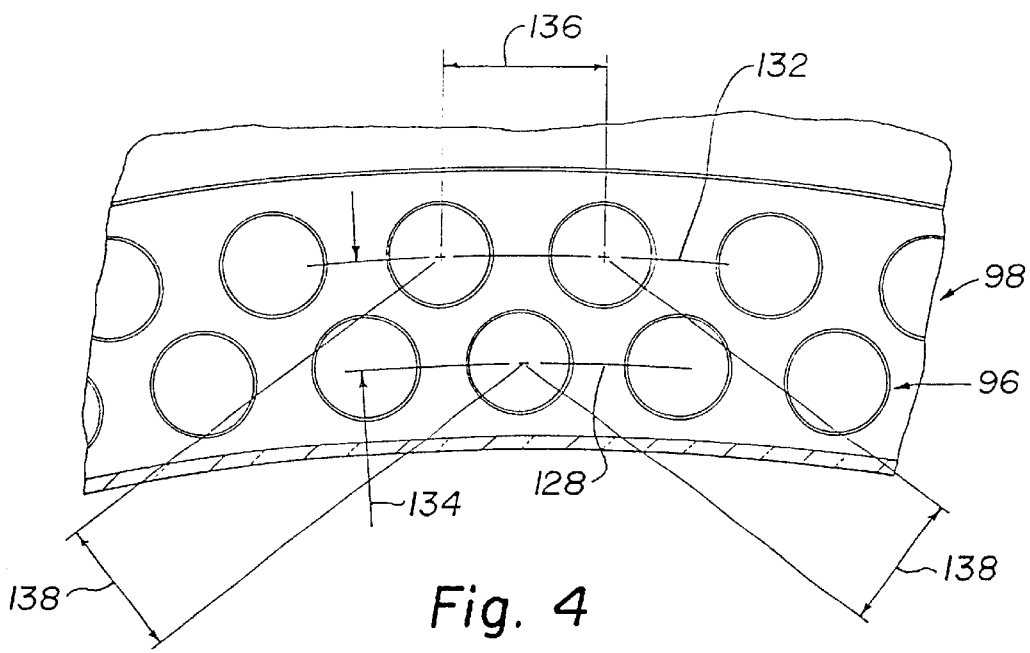
FIG. 4 is a partial sectional view of the upper tanning unit showing the detailed spacing configuration of the tanning bulbs.

The second section 126 of the lamp chamber 92 has a width defined by the centerline 132 that extends between the inner wall portions 116b and 116d, and a depth defined by the same inner wall sections. The width is sufficient to accommodate the desired number of lamps. In the preferred embodiment, the width accommodates a row of lamps 98 having a desired number of T12 100 or T12 160 watt high output tanning lamps 98a-98l positioned on centerline 132 and spaced from about 3° to about 5° apart on about a 32 to 33 inch radius. In the preferred embodiment the lamps 98a-98l depend slightly into the first section 124. The relative spacing of the lamps in the lamp chamber 92 is illustrated in FIG. 4. The lamps 98a-98l in the second row of lamps 98 are positioned above and are centered between the lamps 96a-96t in the first row of lamps 96. This staggered arrangement of the lamps minimizes the diffraction and refraction losses of the ultraviolet energy added to the tanning bed by the second row of lamps 98. The first and second row center lines 128 and 132 are separated by a distance 134 that measures 1.25 to 1.75 inches in the preferred embodiment The center to center spacing 136 between lamps on the same centerline is 2.0–2.5 inches in the preferred embodiment.

To use the invention, a person first moves the upper tanning unit 16 to the open position. Since the first extruded rail 56a is positioned below the horizontal centerline 68, the person can enter the tanning chamber 118 with little or no difficulty, such as by first sitting on the concave sheet 30 and then moving to a prone position. The person then moves the upper tanning unit 16 to the closed position and begins the tanning session, which can be performed more rapidly due to the increased ultraviolet output of the staggered tanning lamps. Furthermore, since at least one tanning lamp is positioned at or near the horizontal centerline 68 on each side of the tanning chamber 118, the person will receive an even distribution of radiation and an even tan along their sides. The person can alternate from lying on his/her stomach to his/her back during the tanning session or from one tanning session to the next to further ensure an even tan.

Figure 5:
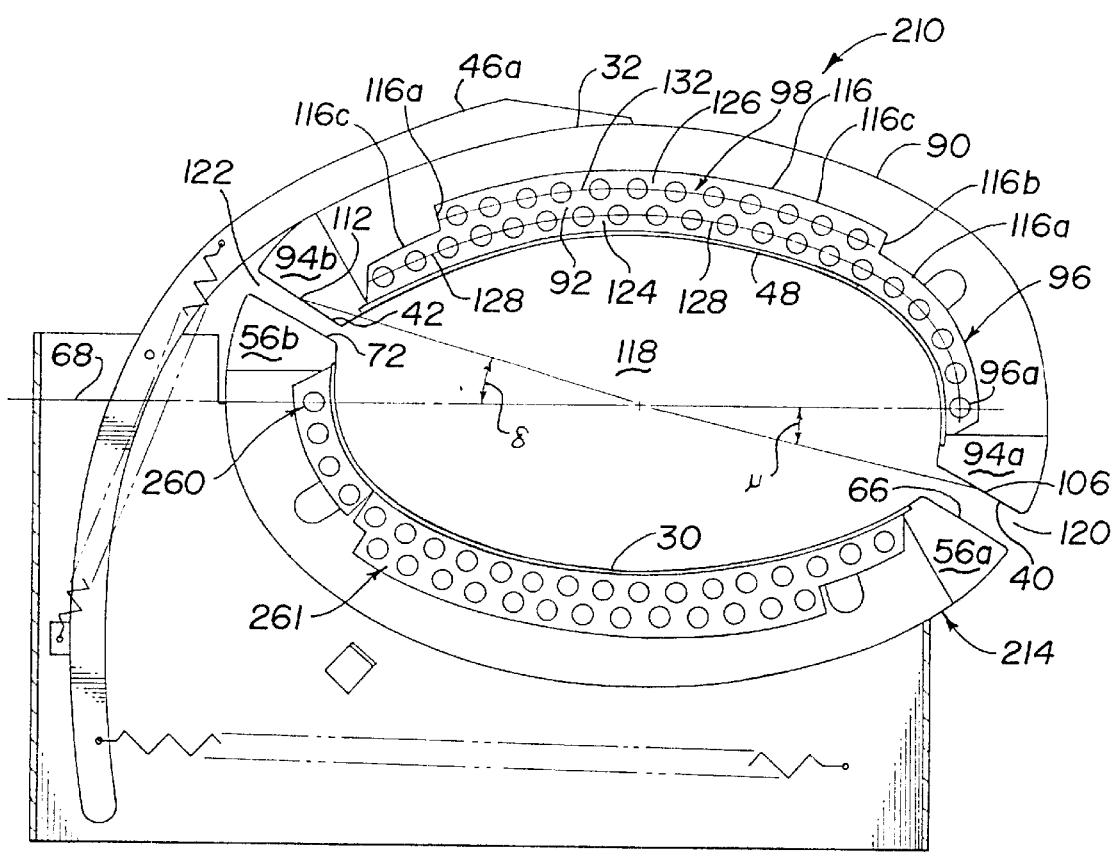
FIG. 5 is a sectional view of another embodiment of the invention wherein the lower tanning unit has a first row of tanning lamps and a second row of tanning lamps.

Referring now to FIG. 5, another embodiment of a tanning bed 210 according to the invention is shown. The tanning bed 210 is substantially the same as the tanning bed 10 previously described herein and includes a lower tanning unit 214 having a first row of tanning lamps 260 and a second row of tanning lamps 261. The first row of tanning lamps 260 and the second row of tanning lamps 261 are staggered with respect to each other.

Although the invention has been described with reference to a preferred embodiment, other embodiments can achieve the same results. Other variations and modifications of the present invention will be apparent to those skilled in the art and can be made without departing from the spirit and scope of the invention as defined by the appended claims.

What is claimed is:

1. An artificial apparatus for tanning a person, the apparatus comprising:
    a lower tanning unit having a lower tanning unit length and a plurality of tanning lamps extending over most of the lower tanning unit length; and
    an upper tanning unit having an upper tanning unit length and having a first and second row of tanning lamps, the lamps of both rows extending over most of the upper tanning unit length.

2. An apparatus as in claim 1 wherein the lamps in the first row are staggered with respect to the lamps in the second row.

3. An apparatus as in claim 1, the lower tanning unit having a first and second row of lower tanning unit lamps.

4. An apparatus as in claim 2, the lower tanning unit having a first and second row of lower tanning unit lamps.

5. An apparatus as in claim 3, wherein the lamps of the first row of the lower tanning unit lamps are staggered with respect to the lamps of the second row of the lower tanning unit lamps.

6. An apparatus as in claim 4, wherein the lamps of the first row of the lower lamps are staggered with respect to the lamps of the second row of the lower tanning 7. An apparatus as in claim 1, wherein the lamps of the first and second rows are of uniform diameter.

* * * * *

UNITED STATES PATENT AND TRADEMARK OFFICE
CERTIFICATE OF CORRECTION

PATENT NO.    : 6,494,901 B1
DATED         : December 17, 2002
INVENTOR(S)   : John Stephen Doty It is certified that error appears in the above-identified patent and that said Letters Patent is hereby corrected as shown below:

<u>Title page,</u>
Item [57], ABSTRACT,
Line 12, after "The" delete -- : --;

<u>Column 1,</u>
Line 20, "ultra violet" should be -- ultraviolet --;
Line 31, after "and" delete "a";
Line 32, after "clamshell" insert a -- . --;
Lines 33 and 55, after "unit" insert a -- . --;
Line 41, delete "users' " and replace it with -- user's --;
Line 42, after "the", second occurrence, delete "S";

<u>Column 2,</u>
Line 1, after "unit" insert -- . An upper tanning unit --;
Line 4, after "unit" insert a -- . --;
Line 9, after "position" insert a -- . --;
Line 26, after "output" insert a -- . --;
Line 29, after "tion" insert a -- . --;
Line 51, after "position;" delete "and";
Line 54, after "bulbs" delete "." and insert -- ; and --;

<u>Column 3,</u>
Line 13, after "12" insert a -- . --;
Lines 14 and 30, "ultra violet" should be -- ultraviolet --;
Line 35, after "device" insert a -- . --;

<u>Column 4,</u>
Line 7, after "centerline" insert a -- . --;

<u>Column 5,</u>
Line 30, delete "6" and insert --  --;
Line 62, after "122" insert -- . --;

UNITED STATES PATENT AND TRADEMARK OFFICE
CERTIFICATE OF CORRECTION

PATENT NO. : 6,494,901 B1
DATED : December 17, 2002
INVENTOR(S) : John Stephen Doty It is certified that error appears in the above-identified patent and that said Letters Patent is hereby corrected as shown below:

<u>Column 8,</u>
Line 15, after "lower" insert -- tanning unit --;
Line 16, after "tanning" insert -- lamps. --.

Signed and Sealed this

Eleventh Day of March, 2003

JAMES E. ROGAN
*Director of the United States Patent and Trademark Office*